US012797359B2

(12) United States Patent
Weinkauf et al.

(10) Patent No.: US 12,797,359 B2
(45) Date of Patent: Nov. 17, 2026

(54) COMPOSITIONS AND METHODS FOR TREATING ACUTE ALCOHOL INTAKE

(71) Applicant: NEXT LEVEL HEALTH SCIENCES INC, Calgary (CA)

(72) Inventors: David Weinkauf, Calgary (CA); Mark Scott, Calgary (CA); Nancy Schmidt, Calgary (CA)

(73) Assignee: NEXT LEVEL HEALTH SCIENCES INC., Calgary (CA)

( * ) Notice: Subject to any disclaimer, the term of this patent is extended or adjusted under 35 U.S.C. 154(b) by 435 days.

(21) Appl. No.: 18/698,010

(22) PCT Filed: Oct. 4, 2022

(86) PCT No.: PCT/IB2022/059478
§ 371 (c)(1),
(2) Date: Apr. 2, 2024

(87) PCT Pub. No.: WO2023/057908
PCT Pub. Date: Apr. 13, 2023

(65) Prior Publication Data

US 2025/0073201 A1 Mar. 6, 2025

Related U.S. Application Data

(60) Provisional application No. 63/252,108, filed on Oct. 4, 2021.

(51) Int. Cl.

| | |
|---|---|
| *A61K 31/352* | (2006.01) |
| *A61K 31/538* | (2006.01) |
| *A61K 36/258* | (2006.01) |
| *A61K 36/33* | (2006.01) |
| *A61K 38/06* | (2006.01) |
| *A61P 25/32* | (2006.01) |

(52) U.S. Cl.
CPC .......... *A61K 31/352* (2013.01); *A61K 31/538* (2013.01); *A61K 36/258* (2013.01); *A61K 36/33* (2013.01); *A61K 38/063* (2013.01); *A61P 25/32* (2018.01)

(58) Field of Classification Search
None
See application file for complete search history.

(56) References Cited

FOREIGN PATENT DOCUMENTS

CN 101721425 A 12/2009

OTHER PUBLICATIONS

Shen et al. "Dihydromyricetin as a novel anti-alcohol intoxication medication" J. Neuroscience, 2012, 32(1), pp. 390-401.*

* cited by examiner

*Primary Examiner* — Po-Chih Chen
(74) *Attorney, Agent, or Firm* — Nexus CP LAW PLC

(57) ABSTRACT

The present disclosure relates to compositions comprising dihydromyricetin (DHM) and fulvic or humic acid or a combination of both, for preventing, ameliorating or treating the effects of acute alcohol intake in a subject. In some embodiments, the composition may further comprise *Opuntia ficus indica* (prickly pear) or *Panax ginseng* or S-acetyl glutathione. The composition may be either a single composition or multiple, smaller compositions.

20 Claims, 1 Drawing Sheet

| | | | Timepoint 1 | | | | | Timepoint 2 | | | | | Timepoint 3 | | | | |
|---|---|---|---|---|---|---|---|---|---|---|---|---|---|---|---|---|---|
| | | | WITH H180 | | | | | WITHOUT H180 | | | | | WITH H180 | | | | |
| | | | Participant | | | | | Participant | | | | | Participant | | | | |
| QUESTIONS | RATE FROM 1-5 (1 BEING NOT AT ALL & 5 BEING SEVERELY) THE DEGREE TO WHICH YOU FEEL THE FOLLOWING | | A | B | C | D | E | A | B | C | D | E | A | B | C | D | E |
| | Headache | 1 to 5 | 1 | 1 | 1 | 2 | 1 | 3 | 4 | 4 | 3 | 3 | 1 | 1 | 2 | 1 | 1 |
| | Nausea | 1 to 5 | 1 | 1 | 1 | 1 | 1 | 1 | 3 | 2 | 1 | 3 | 1 | 1 | 1 | 1 | 1 |
| | Anxiety | 1 to 5 | 1 | 3 | 1 | 2 | 1 | 1 | 5 | 4 | 1 | 4 | 1 | 3 | 1 | 1 | 1 |
| | Fatigue | 1 to 5 | 2 | 3 | 2 | 3 | 1 | 4 | 5 | 3 | 4 | 4 | 2 | 2 | 2 | 3 | 3 |
| | Muscle Pain | 1 to 5 | 2 | 2 | 2 | 1 | 1 | 2 | 4 | 2 | 3 | 3 | 3 | 1 | 1 | 2 | 1 |
| | Thirst | 1 to 5 | 1 | 1 | 1 | 1 | 1 | 1 | 3 | 3 | 3 | 2 | 1 | 2 | 1 | 2 | 2 |
| | Irritability | 1 to 5 | 2 | 1 | 1 | 2 | 1 | 3 | 3 | 2 | 2 | 5 | 1 | 2 | 2 | 2 | 2 |
| | Sweaty | 1 to 5 | 1 | 1 | 1 | 1 | 1 | 3 | 1 | 2 | 4 | 1 | 1 | 1 | 1 | 1 | 2 |
| | Sensitivity to Light and Noise | 1 to 5 | 1 | 2 | 2 | 1 | 1 | 3 | 5 | 4 | 4 | 3 | 1 | 3 | 1 | 1 | 1 |
| | Weakness | 1 to 5 | 1 | 2 | 1 | 1 | 1 | 2 | 4 | 2 | 2 | 3 | 1 | 2 | 1 | 2 | 1 |
| | Regret | 1 to 5 | 1 | 1 | 1 | 1 | 1 | 5 | 5 | 4 | 3 | 5 | 1 | 2 | 1 | 1 | 1 |
| | Optimism | 1 to 5 | 4 | 2 | 3 | 3 | 5 | 1 | 1 | 2 | 2 | 1 | 5 | 4 | 3 | 4 | 4 |

COMPOSITIONS AND METHODS FOR TREATING ACUTE ALCOHOL INTAKE

RELATED APPLICATIONS

This application claims priority to and the benefit of U.S. Provisional Patent Application Ser. No. 63/252,108, filed Oct. 4, 2021, and entitled "COMPOSITIONS AND METHODS FOR TREATING ACUTE ALCOHOL INTAKE", the disclosure of which is incorporated hereby reference in its entirety.

FIELD

The present disclosure relates generally to compositions for treating acute alcohol intake and methods of using the same.

BACKGROUND

Alcohol is the most widely used addictive drug in the United States. In 2019, nearly 26% of adults reported that they engaged in heavy alcohol use, or binge drinking, in the past month. Emerging trends indicate that high-intensity drinking has grown in the United States. Between 2006 and 2014, alcohol-related emergency room hospital visits averaged an annual increase of roughly 210,000 visits. Compared to casual drinkers, individuals who drank alcohol at twice the gender-specific binge drinking thresholds were 70 times more likely to have an alcohol-related emergency room hospital visit. Those who consumed alcohol at three times the thresholds were 93 times more likely to have an emergency room visit. In fact, alcohol contributed to about 19% of all emergency department visits and 22% of all overdose deaths related to prescription opioids. The confluence of these factors has made alcohol the third-leading preventable cause of death in the United States. The economic burden of alcoholism has been substantial, costing the United States $259 billion in 2010. The consequences for families are even greater. Nearly 11% of U.S. children 17 and younger live with a parent with Alcohol Use Disorder (AUD). AUD is defined as a chronic brain disorder indicated by compulsive drinking, loss of control over alcohol use, and poor emotional behavior in the absence of alcohol. AUD development is believed to be caused by both genetic and environmental influences on the human brain.

Acute negative effects of compulsive drinking may include sudden swings in mood, impaired judgment, slurred speech, impaired attention or memory, and poor coordination. Effects may range from mild, such as skin flushing, to severe, such as vomiting, "blackouts," coma, and even death. Acute alcohol intake is also associated with hangovers. Symptoms from hangovers can include fatigue, excessive thirst, nausea, dizziness, shakiness, decreased ability to concentrate, and rapid heartbeat, amongst others. Acute alcohol intake can also result in alcohol poisoning, which can be life-threatening. Thus, there exists a need in the art to treat acute alcohol intake.

SUMMARY

In an aspect, a composition is provided for treating acute alcohol intake comprising an amount of dihydromyricetin (DHM), and an amount of fulvic acid, humic acid, or a combination of both fulvic acid and humic acid.

In embodiments, the composition includes an amount of humic acid. In embodiments, the composition includes an amount of *Opuntia ficus indica*. In embodiments, the composition includes an amount of *Panax ginseng*. In embodiments, the composition includes an amount of S-acetyl-glutathione. The composition may be provided as a single composition or multiple, smaller compositions (e.g., in a gummy form).

In embodiments, the DHM is present in an amount of about 100 mg to about 5000 mg. In further embodiments, the DHM is present in an amount of about 1500 mg. In embodiments, the fulvic acid is present in an amount of about 30 mg to about 3000 mg. In embodiments, the fulvic acid is present in an amount of about 600 mg. In embodiments, the humic acid is present in an amount of about 30 mg to about 3000 mg. In embodiments, the humic acid is present in an amount of about 600 mg. In embodiments, the combination of fulvic acid and humic acid is present in an amount of about 30 mg to about 3000 mg. In embodiments, the combination of fulvic acid and humic acid is present in an amount of about 600 mg.

In embodiments, the *Opuntia ficus indica* is present in an amount of about 50 mg to about 1000 mg. In embodiments, the *Panax ginseng* is present in an amount of about 25 mg to about 2000 mg.

In embodiments, the S-acetyl-glutathione is present in an amount of about 1 mg to about 2000 mg. In embodiments, the S-acetyl-glutathione is present in an amount of about 75 mg.

In another aspect, a composition is disclosed comprising about 1500 mg of dihydromyricetin (DHM); about 600 mg of a combination of fulvic acid and humic acid; and about 75 mg of S-acetyl-glutathione.

In an aspect, a method is provided comprising preventing, ameliorating or treating effects of alcohol consumption in a subject, the method comprising administering an effective amount of any of the compositions disclosed herein.

In an aspect, a kit is provided comprising any of the compositions disclosed herein in one or more unit dose forms, and instructions for use of the composition.

BRIEF DESCRIPTION OF THE DRAWINGS

In this Application:

FIG. 1 depicts a summary of data with and without administration of the composition according to an embodiment of this disclosure.

DETAILED DESCRIPTION

Overview

The present disclosure relates to compositions for treating acute alcohol intake. In certain embodiments, the compositions comprise the components of dihydromyricetin (DHM) and fulvic acid, humic acid, or a combination of both. In certain embodiments, methods are provided that comprise administering the compositions disclosed herein.

Description of Aspects and Embodiments of the Disclosure

In an aspect a composition is provided comprising an amount of at least one botanical extract, and an acid. In an aspect, a composition is provided for treating acute alcohol intake comprising an amount of dihydromyricetin (DHM), and an acid. In embodiments, the DHM is from *Ampelopsis grossedentata*. In embodiments, the DHM is from *Hovenia dulcis*. In embodiments, the DHM is from *Ampelopsis*

*grossedentata* and *Hovenia dulcis*. In embodiments, the acid comprises fulvic acid, humic acid, or a combination of both.

In embodiments, a dosage range of DHM in the composition comprises between 100 mg and 5000 mg, for example, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, at least 2900 mg, at least 3000 mg, at least 3100 mg, at least 3200 mg, at least 3300 mg, at least 3400 mg, at least 3500 mg, at least 3600 mg, at least 3700 mg, at least 3800 mg, at least 3900 mg, at least 4000 mg, at least 4100 mg, at least 4200 mg, at least 4300 mg, at least 4400 mg, at least 4500 mg, at least 4600 mg, at least 4700 mg, at least 4800 mg, or at least 4900 mg. In certain embodiments a dosage of DHM in the composition comprises 1500 mg.

In embodiments, a dosage range of fulvic acid in the composition comprises between 30 mg and 3000 m, for example at least 30 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, or at least 2900 mg. In embodiments, a dosage of fulvic acid in the composition comprises 600 mg.

In embodiments, a dosage range of humic acid in the composition comprises between 30 mg and 3000 mg, for example at least 30 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, or at least 2900 mg. In embodiments, a dosage of humic acid in the composition comprises 600 mg.

In embodiments, a dosage range of a humic/fulvic acid combination in the composition comprises between 30 mg and 3000 mg, for example at least 30 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, or at least 2900 mg. In embodiments, a dosage of the humic/fulvic acid combination in the composition comprises 600 mg.

In certain embodiments, a dosage of prickly pear cactus (also referred to herein as *Opuntia ficus indica*) is included in the composition comprising between 50 mg and 1000 mg, for example, at least 50 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, or at least 2000 mg. In embodiments, a dosage of prickly pear cactus in the composition comprises 500 mg.

In certain embodiments, a dosage of *Panax ginseng* in the composition comprises between 25 mg and 2000 mg, for example, at least 25 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, or at least 1900 mg. In embodiments, a dosage of *Panax ginseng* in the composition comprises 200 mg.

In embodiments, a dosage of S-Acetyl-Glutathione in the composition comprises between 1 mg and 2000 mg, for example, at least 1 mg, at least 10 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, or at least 1900 mg. In embodiments, a dosage of S-Acetyl-Glutathione in the composition comprises 75 mg.

In embodiments, the composition further comprises at least one vitamin. In embodiments, the at least one vitamin comprises Vitamin B. In embodiments, the Vitamin B comprises Vitamin B1. In embodiments, Vitamin B1 comprises Thiamine Hydrochloride. In embodiments, the Vitamin comprises Vitamin B3. In embodiments, Vitamin B3 comprises Niacinamide. In embodiments, the Vitamin comprises Vitamin B6. In embodiments, Vitamin B6 comprises Pyridoxine Hydrochloride.

In embodiments, a dosage of Vitamin B1 in the composition comprises between 5 mg and 500 mg, for example at least 5 mg, at least 100 mg, at least 200 mg, at least 300 mg, or at least 400 mg. In embodiments, a dosage of Vitamin B1 in the composition comprises 100 mg.

In embodiments, a dosage of Vitamin B3 in the composition comprises between 10 mg and 1500 mg, for example, at least 10 mg, at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, or at least 1400 mg. In embodiments, a dosage of Vitamin B3 in the composition comprises 100 mg.

In embodiments, a dosage of Vitamin B6 in the composition comprises between 5 mg and 500 mg, for example, at least 5 m, at least 100 mg, at least 200 mg, at least 300 mg, or at least 400 mg. In embodiments, a dosage of Vitamin B6 in the composition comprises 100 mg.

In additional embodiments, an amount of acetyl-L-carnitine is included in the composition in an amount ranging from about 50 mg to about 2000 mg.

In additional embodiments, an amount of L-theanine (e.g., *Camellia sinensis*) is included in the composition in an amount ranging from about 25 mg to about 250 mg.

In additional embodiments, an amount of DL-alpha-lipoic acid is included in the composition in an amount ranging from about 50 mg to about 600 mg.

In additional embodiments, an amount of kudzu (e.g., *Pueraria* lobate) is included in the composition in an amount ranging from about 400 mg to about 4000 mg.

In additional embodiments, an amount of skullcap (e.g., *Scutellaria baicalensis*) is included in the composition in an amount ranging from about 200 mg to about 2000 mg.

In additional embodiments, an amount of milk thistle (e.g., *Silybum marianum*) is included in the composition in an amount ranging from about 50 mg to about 1000 mg.

In additional embodiments, an amount of bacopa (e.g., *Bacopa monnieri*) is included in the composition in an amount ranging from about 100 mg to about 1000 mg.

In additional embodiments, an amount of gotu kola (e.g., *Centella asiatica*) is included in the composition in an amount ranging from about 100 mg to about 3000 mg.

In additional embodiments, an amount of ashwagandha (e.g., *Withania somnifera*) is included in the composition in an amount ranging from about 200 mg to about 5000 mg.

In additional embodiments, an amount of green tea extract (e.g., *Camellia sinensis*) is included in the composition in an amount ranging from about 300 mg to about 2500 mg.

In additional embodiments, an amount of magnesium is included in the composition in an amount ranging from about 10 mg to about 350 mg.

In additional embodiments, an amount of zinc is included in the composition in an amount ranging from about 5 mg to about 50 mg.

In additional embodiments, an amount of selenium is included in the composition in an amount ranging from about 5 μg to about 200 μg.

In embodiments, the compositions described herein can be in the form of a gummy or a capsule.

In an aspect, a method is provided for producing and packaging a capsule. In embodiments, the method comprises (i) scaling formula to 5-10% over the amount needed for production; (ii) collecting all ingredients and verifying the proper identity and quantities available; (iii) scaling all ingredients according to a production formula; (iv) blending all ingredients in a single container until the mixture is homogenous (the type of mixer used depends on the size of the batch being produced); (v) prepping a work station and capsule presses to ensure conditions are sanitary and devoid of moisture; (vi) beginning to fill capsules and checking fill weights with each press; (vii) filling capsules and checking weights throughout the run to ensure that there is very little to no sway in the weights; (viii) dusting all finished capsules to remove powders that have adhered to the surface during production, (ix) storing all capsules in an air tight container until ready for packaging, (x) packaging all finished capsules in the packaging provided and sealing to ensure product safety and stability, and (xi) packaging all sealed bags/pouches of capsules into boxes for shipping.

In an aspect, a method is provided for producing and packaging gummies. In embodiments, ingredients included in the method may comprise cane sugar, glucose syrup, water, fructose, pectin, *Cordyceps sinensis* mycelium powder, citric acid, natural and artificial flavoring, potassium sorbate, sucralose, colors from natural sources (e.g., vegetable juice).

In a particular aspect, the active ingredients are fulvic acid, DHM, SAG (S-Acetyl-Glutathione). In embodiments, the procedure for producing and packaging the gummies includes the following steps: combine pectin, sugar, bitter blocker, fructose, sucralose. This combination is added to water, mixed thoroughly until the texture is smooth. Then, add hot glucose to mixture and mix until uniform. Once all the powders are dissolved and the slurry reaches between 30° C. and 100° C., begin incorporating DHM. In embodiments, the slurry will reach at least 30° C. In embodiments, the slurry will reach at least 40° C. In embodiments, the slurry will reach at least 50° C. In embodiments, the slurry will reach at least 60° C. In embodiments, the slurry will reach at least 70° C. In embodiments, the slurry will reach at least 80° C. In embodiments, the slurry will reach at least 90° C. In embodiments, the slurry will reach at least 100° C. Then, once the slurry reaches target BRIX value, add all active ingredients, natural flavors and the acid, and mix thoroughly until uniform. Then, pour the gummy slurry onto molds ensuring that all cavities are filled evenly. Then, once the gummies have set, demold and sand with sugar/flavor blend. Then, spread the gummies evenly on sheet pans and allow to cure for a minimum of 24-48 hours. Then, package the gummies in a bag.

In an aspect, methods are providing for treating acute alcohol intake comprising administering any of the compositions described herein.

In embodiments, the composition described herein are provided in the form of a tablet, capsule, gummy, pill, liquid, powder for mixing, or patch designed to be temporarily affixed to the skin for transdermal migration. The capsule delivery system contains the powder form of each substance. In another exemplary embodiment, the compositions described herein are a liquid concentrate. Such a liquid concentrate may, for example, be used as a mixer in a cocktail. The term "mixer," within the context of the present invention, refers to a non-alcoholic beverage, such as sour mix, simple syrup, mojito mix, daiquiri mix, margarita mix, etc., which is conventionally used as a component or additive in cocktails. Exemplary, non-limiting examples of mixers can be found in bartending manuals. In one exemplary embodiment, the compositions described herein are a carbonated beverage.

In one exemplary embodiment, the compositions described herein is/are administered multiple times surrounding the period of time when the person is consuming alcoholic beverages, such as, for example, one or more times during any of the times prior to, during, and after the person is consuming alcoholic beverages.

The composition is formulated by mixing the compounds listed above and encapsulating the composition into capsules. In one embodiment, each capsule contains the listed amount of each compound in Table 1 below.

The synergistic effect between the botanical extract and the other compounds in the present disclosure provides a significant improvement over the state of the art for treating the effects of alcohol consumption.

An "effective amount" (or alternately, a "therapeutically effective amount") is an amount that alone, or together with further doses, produces the desired (therapeutic) response. The (therapeutically) effective amount to be used will depend, for example, upon the therapeutic objectives, the route of administration, and the condition of the person.

A suitable dosage of the compositions described herein for a given person can be determined by taking into consideration various factors known to modify the action of the ingredients including body weight, sex, diet, time and route of administration, other medications and other relevant clinical factors. Accordingly, in one example, a suitable dose is selected based on the body weight of the person. The dosages and schedules may be varied according to the overall condition of the person. Suitable doses may also be determined based on the alcohol consumption levels of the person.

The compositions described herein are therefore administered to a person in an effective amount to produce the desired response. Examples of such responses include thirst, fatigue, headache, dizziness/faintness, loss of appetite, stomach ache, nausea, poor and/or decreased sleep, and elevated heart rate.

EXAMPLES

Example 1. Testing of Composition Components

To test, various components of the compositions disclosed herein, individuals were selected to test the efficacy of various formulations.

The scale employed during the testing of alcohol-induced symptoms was as follows: (a) no symptoms; (b) very mild symptoms; (c) mild symptoms; (d) moderate symptoms; (e) severe symptoms; and/or (f) very severe symptoms.

During testing, it was established that benefits of DHM on hangover symptoms begin at a dosage of about 300 mg and that no additional benefits were seen above about 1850 mg. The testing was carried out by a man of average size and build consuming standard alcoholic drinks (e.g., a beer) and the components below were consumed generally prior to consumption of alcohol. The testing results follow:

3 drinks without DHM resulted in very mild symptoms.

3 drinks with less than 300 mg of DHM resulted in no reduction of symptoms.

3 drinks with 300 mg of DHM resulted in an elimination of all symptoms.

6 drinks without DHM resulted in moderate symptoms.

6 drinks with 300 mg of DHM resulted in a reduction to mild symptoms.

6 drinks with 750 mg of DHM resulted in a reduction to very mild symptoms.

6 drinks with 1200 mg of DHM resulted in an elimination of all symptoms.

9 drinks without DHM resulted in severe symptoms.

9 drinks with 300 mg of DHM resulted in no reduction of symptoms.

9 drinks with 750 mg of DHM resulted in a reduction to moderate symptoms.

9 drinks with 1200 mg of DHM resulted in a reduction to mild symptoms.

9 drinks with 1500 mg of DHM resulted in a reduction to very mild symptoms.

9 drinks with 1850 mg of DHM resulted in a reduction of all symptoms with the sole exception of fatigue.

12 drinks without DHM resulted in severe symptoms.

12 drinks with 750 mg of DHM resulted in no reduction of symptoms.

12 drinks with 1200 mg of DHM resulted in no reduction of symptoms.

12 drinks with 1500 mg of DHM resulted in a reduction to moderate symptoms.

12 drinks with 1850 mg of DHM resulted in no further reduction in symptoms.

12 drinks with 2400 mg of DHM resulted in no further reduction in symptoms.

15 drinks without DHM resulted in very severe symptoms.

15 drinks with 1500 mg of DHM resulted in no reduction of symptoms.

15 drinks with 1850 mg of DHM resulted in a reduction to severe symptoms.

15 drinks with 2400 mg of DHM resulted in no further reduction of symptoms.

15 drinks with 3600 mg of DHM resulted in no further reduction of symptoms.

18 drinks without DHM resulted in very severe symptoms.

18 drinks with 1850 mg of DHM resulted in no reduction of symptoms.

18 drinks with 2400 mg of DHM resulted in no reduction of symptoms.

18 drinks with 3600 mg of DHM resulted in no reduction of symptoms.

18 drinks with 5000 mg of DHM resulted in no reduction of symptoms.

Having determined that DHM plays a role in ameliorating symptoms associated with acute alcohol consumption, additional ingredients/components were tested.

Testing was carried out using 12 and 15 drinks because it had previously been determined that no dose of DHM, as tested, eliminated all symptoms. The testing was as follows:

12 drinks with 1500 mg of prickly pear extract had no impact on symptoms.

15 drinks with 1500 mg of prickly pear extract had no impact on symptoms.

12 drinks with 1500 mg of milk thistle extract had no impact on symptoms.

15 drinks with 1500 mg of milk thistle extract had no impact on symptoms.

12 drinks with 300 mg of *Panax ginseng* had no impact on symptoms.

15 drinks with 300 mg of *Panax ginseng* had no impact on symptoms.

12 drinks with 1000 mg of V-Vitamin Complex had no impact on symptoms.

15 drinks with 1000 mg of V-Vitamin Complex had no impact on symptoms.

12 drinks with 1000 mg of green tea extract had no impact on symptoms.

15 drinks with 1000 mg of green tea extract had no impact on symptoms.

When testing S-Acetyl-Glutathione, the following testing was performed and the following data was collected.

12 drinks with 300 mg of S-Acetyl-Glutathione combined with 750 mg of DHM resulted in no reduction in symptoms.

12 drinks with 300 mg of S-Acetyl-Glutathione combined with 1200 mg of DHM resulted in a reduction to moderate symptoms. Importantly, this resulted in a decrease in 300 mg of DHM to show the same efficacy as with DHM alone.

12 drinks with 300 mg of S-Acetyl-Glutathione combined with 1500 mg of DHM resulted in no further reduction of symptoms.

12 drinks with 300 mg of S-Acetyl-Glutathione combined with 1850 mg of DHM resulted in no further reduction of symptoms.

12 drinks with 300 mg of S-Acetyl-Glutathione combined with 2400 mg of DHM resulted in no further reduction of symptoms.

15 drinks with 300 mg of S-Acetyl-Glutathione combined with 1500 mg of DHM resulted in a reduction to severe symptoms. Importantly, this resulted in a decrease in 350 mg of DHM to show the same efficacy as with DHM alone.

15 drinks with 300 mg of S-Acetyl-Glutathione combined with 1850 mg of DHM resulted in no further reduction of symptoms.

15 drinks with 300 mg of S-Acetyl-Glutathione combined with 2400 mg of DHM resulted in no further reduction of symptoms.

15 drinks with 300 mg of S-Acetyl-Glutathione combined with 3600 mg of DHM resulted in no further reduction of symptoms.

When testing humic-fulvic acid, the following testing was performed and the following data was collected.

12 drinks with 3000 mg of humic-fulvic acid combined with 750 mg of DHM resulted in no reduction of symptoms.

12 drinks with 3000 mg of humic-fulvic acid combined with 1200 mg of DHM resulted in a reduction to moderate symptoms. Importantly, this resulted in a decrease in 300 mg of DHM to show the same efficacy as with DHM alone.

12 drinks with 3000 mg of humic-fulvic acid combined with 1500 mg of DHM resulted in no further reduction of symptoms.

12 drinks with 3000 mg of humic-fulvic acid combined with 1850 mg of DHM resulted in a reduction to mild symptoms. Importantly, this resulted in a decrease of at least one level on the scale of symptoms over DMH alone.

12 drinks with 3000 mg of humic-fulvic acid combined with 2400 mg of DHM resulted in no further reduction of symptoms.

15 drinks with 3000 mg of humic-fulvic acid combined with 1200 mg of DHM resulted in a reduction to severe symptoms. Importantly, this resulted in a decrease in 850 mg of DHM to show the same efficacy as with DHM alone.

15 drinks with 3000 mg of humic-fulvic acid combined with 1500 mg of DHM resulted in no further reduction of symptoms.

15 drinks with 3000 mg of humic-fulvic acid combined with 1850 mg of DHM resulted in a reduction to moderate symptoms. Importantly, this resulted in a decrease of at least one level on the scale of symptoms over DMH alone.

15 drinks with 3000 mg of humic-fulvic acid combined with 2400 mg of DHM resulted in no further reduction of symptoms.

15 drinks with 3000 mg of humic-fulvic acid combined with 3600 mg of DHM resulted in no further reduction of symptoms.

Testing of kudzu was also carried out. The testing was as follows:

12 drinks with 450 mg of kudzu had no impact on symptoms.

15+ drinks with 450 mg of kudzu had no impact on symptoms.

Testing of N-Acetyl-Cysteine was also carried out. The testing was as follows:

12 drinks with 1000 mg of N-Acetyl-Cysteine combined with 750 mg of DHM resulted in a reduction to moderate symptoms. Importantly, this resulted in a decrease in 750 mg of DHM to show the same efficacy as with DHM alone.

12 drinks with 1000 mg of N-Acetyl-Cysteine combined with 1200 mg of DHM resulted in a reduction to mild symptoms. Importantly, this resulted in a decrease of at least one level on the scale of symptoms over DMH alone.

12 drinks with 1000 mg of N-Acetyl-Cysteine combined with 1500 mg of DHM resulted in no further reduction of symptoms.

12 drinks with 1000 mg of N-Acetyl-Cysteine combined with 1850 mg of DHM resulted in no further reduction of symptoms.

12 drinks with 1000 mg of N-Acetyl-Cysteine combined with 2400 mg of DHM resulted in no further reduction of symptoms.

15 drinks with 1000 mg of N-Acetyl-Cysteine combined with 1200 mg of DHM resulted in a reduction to severe symptoms. Importantly, this resulted in a decrease in 850 mg of DHM to show the same efficacy as with DHM alone.

15 drinks with 1000 mg of N-Acetyl-Cysteine combined with 1500 mg of DHM resulted in a reduction to moderate symptoms. Importantly, this resulted in a decrease of at least one level on the scale of symptoms over DMH alone.

15 drinks with 1000 mg of N-Acetyl-Cysteine combined with 1850 mg of DHM resulted in no further reduction of symptoms.

15 drinks with 1000 mg of N-Acetyl-Cysteine combined with 2400 mg of DHM resulted in no further reduction of symptoms.

15 drinks with 1000 mg of N-Acetyl-Cysteine combined with 3600 mg of DHM resulted in no further reduction of symptoms.

Based on obtained results, a series of preferred formulations were produced as follows:

Formulation Ratio A contained: 1850 mg DHM/1000 mg humic & fulvic acid/300 mg S-acetyl Glutathione. The results from experimental tests were as follows:

12 drinks with Formulation Ratio A eliminated all symptoms except fatigue.

15 drinks with Formulation Ratio A eliminated all symptoms except fatigue.

Formulation Ratio B contained: 1500 mg DHM/1000 mg humic & fulvic acid/300 mg S-acetyl Glutathione. The results from experimental tests were as follows:

12 drinks with Formulation Ratio B eliminated all symptoms except fatigue.

15 drinks with Formulation Ratio B reduced all symptoms to very mild symptoms.

Formulation Ratio C contained: 1200 mg DHM/1000 mg humic & fulvic acid/300 mg S-acetyl Glutathione. The results from experimental tests were as follows:

12 drinks with Formulation Ratio C reduced all symptoms to very mild symptoms.

15 drinks with Formulation Ratio C reduced all symptoms to moderate symptoms.

Formulation Ratio D contained: 1500 mg DHM/500 mg humic & fulvic acid/150 mg S-acetyl Glutathione. The results from experimental tests were as follows:

12 drinks with Formulation Ratio D eliminated all symptoms except fatigue.

15 drinks with Formulation Ratio D reduced all symptoms to very mild symptoms.

Formulation Ratio E contained: 1500 mg DHM/300 mg humic & fulvic acid/50 mg S-acetyl Glutathione. The results from experimental tests were as follows:

12 drinks with Formulation Ratio E eliminated all symptoms except fatigue.

15 drinks with Formulation Ratio E reduced all symptoms to mild symptoms.

Example 2. Production of Representative Composition

A composition according an embodiment of the present disclosure (and also referred to herein as HANGOVR-180™) contains the dosages and dosage ranges as listed in Table 1.

TABLE 1

Base Formula Dosage Ranges (HANGOVR-180 ™)

| HANGOVR-180 ™ Ingredients-Base Formula | Dosage (mg) per serving | Dosage Ranges (mg) Minimum | Maximum |
|---|---|---|---|
| Essential Ingredients | | | |
| Dihydromyricetin (DHM) Ampelopsis grossedentata or Hovenia dulcis | 1500 | 300 | 5000 |
| Humic and Fulvic Acid | 600 | 30 | 3000 |
| S-Acetyl-Glutathione | 75 | 0 | 2000 |

Example 3. Capsule Production and Packaging Procedure

The compositions described herein can be in the form of capsules. Capsules can be produced and packaged using the following procedure.

1. Scale formula to 5-10% over the amount needed for production.
2. Collect all ingredients, verifying proper identity and quantities available.
3. Scale all ingredients according to production formula.
4. Blend all ingredients in a single container until homogenous. The type of mixer used is dependent on the size of the batch being produced.
5. Prepare a work station and capsule presses to ensure conditions are sanitary and devoid of moisture.
6. Begin filling capsules, making sure to check fill weights with each press.
7. Fill capsules, checking weights throughout run to ensure there is very little to no sway in weights.
8. Dust all finished capsules to remove powders that have adhered to the surface during production.
9. Store all capsules in air tight container until ready for packaging.
10. Package all finished capsules in packaging provided, and seal to ensure product safety and stability.
11. Package all sealed bags/pouches of capsules into boxes for shipping.

Example 4. Gummy Production Procedure

The compositions described herein can be in the form of gummies. Ingredients for producing gummies include: water, grape juice, glucose, fulvic/humic Acid, DHM, SAG, food coloring, natural flavors, bitter blocker, acid, stevia. Gummy compositions can be produced and packaged using the following procedure.

1. Combine 2 parts sugar with 1 part pectin. Add to water, grape juice, and Bordeaux color and mix thoroughly until smooth in texture.
2. Add hot glucose to mixture and mix until uniform.
3. Slowly add sugar to the mixture until completely dissolved.
4. Once slurry is uniform in color, add all dry ingredients, minus DHM, and mix until uniform.
5. Once all powders are dissolved and the slurry reaches 70° C., begin incorporating DHM. Caution not to exceed 100° C.
6. Once slurry reaches target BRIX value, add all natural flavors and fulvic acid and mix thoroughly until uniform.
7. Pour gummy slurry onto molds ensuring that all cavities are filled evenly.
8. Once gummies have set, demold and sand with sugar/flavor blend.
9. Spread gummies evenly on sheet pans and allow to cure for a minimum of 24-48 hours.
10. Package gummies; 6 per bag.

Example 5. Composition Testing

To test the composition outlined in Table 1 herein, a rating system was employed as follows. Briefly, individuals were asked to rate the degree to which they felt a particular symptom according to the following scale: 1=not at all; 2=mildly; noticeable but not particularly bothersome; 3=moderately; bothersome and uncomfortable but not incapacitating; 4=partially incapacitating, distracting and very uncomfortable; and 5=incapacitating, painful, prevents normal activity entirely.

The protocol was as follows:

Wednesday night of 1st and 3rd week; 4:30 PM—Consume 1 package of H180 (formulation from Table 1); 6:30 PM—Begin consuming alcohol; 9:30 PM—Complete last beverage.

Wednesday night of 2nd week; 6:30 PM—Begin consuming alcohol; 9:30 PM—Complete last beverage.

Thursday morning of all 3 weeks; 8:00 AM—Complete questionnaire according to the above rating system.

The participants were as follows:

Participant A: 67 Years Old—Male—Weight 165 lbs. Personal Consumption Target: 6×355 ml beer (4.4% alcohol by volume).

Participant B: 51 Years Old—Female—Weight 155 lbs. Personal Consumption Target: 4×355 ml gin drink (5% alcohol by volume).

Participant C: 47 Years Old—Male—Weight 185 lbs. Personal Consumption Target: 6×473 ml beer (6.8% alcohol by volume).

Participant D: 45 Years Old—Male—Weight 265 lbs. Personal Consumption Target: 4×355 ml beer (5% alcohol by volume).

Participant E: 48 Years Old—Female—Weight 190 lbs. Personal Consumption Target: 1×750 mL red wine (13.5% alcohol by volume).

The results from these studies are depicted in FIG. 1. Briefly, in the Timepoint 1 studies with the composition from Table 1, the following participants exhibited the following scores for the various symptoms associated with acute alcohol consumption: Participant A exhibited scores of 1, 1, 1, 2, 2, 1, 2, 1, 1, 1, 1, 4. Participant B exhibited scores of 1, 1, 3, 3, 2, 1, 1, 1, 2, 2, 1, 2. Participant C exhibited scores of 1, 1, 1, 2, 2, 1, 1, 1, 2, 1, 1, 3. Participant D exhibited scores of 2, 1, 2, 3, 1, 1, 2, 1, 1, 1, 1, 3. Participant E exhibited scores of 1, 1, 1, 1, 1, 1, 1, 1, 1, 1, 1, 5.

In the negative control studies from Timepoint 2, the following participants exhibited the following scores for the various symptoms associated with acute alcohol consumption: Participant A exhibited scores of 3, 1, 1, 4, 2, 1, 3, 3, 3, 2, 5, 1. Participant B exhibited scores of 4, 3, 5, 5, 4, 3, 3, 1, 5, 4, 5, 1. Participant C exhibited scores of 4, 2, 4, 3, 2, 3, 2, 2, 4, 2, 4, 2. Participant D exhibited scores of 3, 1, 1, 4, 3, 3, 2, 4, 4, 2, 3, 2. Participant E exhibited scores of 3, 3, 4, 4, 3, 2, 5, 1, 3, 3, 5, 1.

In the Timepoint 2 studies with the composition from Table 1, the following participants exhibited the following scores for the various symptoms associated with acute alcohol consumption: Participant A exhibited scores of 1, 1, 1, 2, 3, 1, 1, 1, 1, 1, 1, 5. Participant B exhibited scores of 1, 1, 3, 2, 1, 2, 2, 1, 3, 2, 2, 4. Participant C exhibited scores of 2, 1, 1, 2, 1, 1, 2, 1, 1, 1, 1, 3. Participant D exhibited scores of 1, 1, 1, 3, 2, 2, 2, 1, 1, 2, 1, 4. Participant E exhibited scores of 1, 1, 1, 3, 1, 2, 2, 2, 1, 1, 1, 4.

What is claimed is:

1. A composition for treating acute alcohol intake comprising:

an effective amount of dihydromyricetin (DHM); and an effective amount of fulvic acid, humic acid, or a combination of both fulvic acid and humic acid.

2. The composition of claim 1, further comprising an effective amount of *Opuntia ficus indica*.

3. The composition of claim 1, further comprising an effective amount of *Panax ginseng*.

4. The composition of claim 1, further comprising an effective amount of S-acetyl-glutathione.

5. The composition of claim 1, wherein the DHM is present in an amount of about 100 mg to about 5000 mg.

6. The composition of claim 1, wherein the DHM is present in an amount of about 1500 mg.

7. The composition of claim 1, wherein the fulvic acid is present in an amount of about 30 mg to about 3000 mg.

8. The composition of claim 1, wherein the fulvic acid is present in an amount of about 600 mg.

9. The composition of claim 1, wherein the humic acid is present in an amount of about 30 mg to about 3000 mg.

10. The composition of claim 1, wherein the humic acid is present in an amount of about 600 mg.

11. The composition of claim 1, wherein the combination of fulvic acid and humic acid is present in an amount of about 30 mg to about 3000 mg.

12. The composition of claim 1, wherein the combination of fulvic acid and humic acid is present in an amount of about 600 mg.

13. The composition of claim 2, wherein the *Opuntia ficus indica* is present in an amount of about 50 mg to about 1000 mg.

14. The composition of claim 3, wherein the *Panax ginseng* is present in an amount of about 25 mg to about 2000 mg.

15. The composition of claim 4, wherein the S-acetyl-glutathione is present in an amount of about 1 mg to about 2000 mg.

16. The composition of claim 4, wherein the S-acetyl-glutathione is present in an amount of about 75 mg.

17. A composition for treating acute alcohol intake comprising:

about 1500 mg of dihydromyricetin (DHM);

about 600 mg of fulvic acid, humic acid, or a combination of both fulvic acid and humic acid; and about 75 mg of S-acetyl-glutathione.

18. A method of preventing, ameliorating or treating effects of alcohol consumption in a subject, the method comprising administering an effective amount of the composition of claim 1.

19. A kit comprising a composition according to claim 1 in one or more unit dose forms, and instructions for use of the composition.

20. A kit comprising a composition in one or more unit dose forms comprising:

about 1500 mg of dihydromyricetin (DHM);

about 600 mg of fulvic acid, humic acid, or a combination of both fulvic acid and humic acid; and about 75 mg of S-acetyl-glutathione;

and instructions for use of the composition.

* * * * *